United States Patent [19]

Kamprad et al.

[11] Patent Number: 5,216,019

[45] Date of Patent: Jun. 1, 1993

[54] PAIN KILLER

[76] Inventors: Joachim Kamprad, Kemperweg 67; Ludger Rolf, Hegerskamp 94, both of, D-4400 Munster, Fed. Rep. of Germany

[21] Appl. No.: 865,822

[22] Filed: Apr. 1, 1992

Related U.S. Application Data

[63] Continuation of Ser. No. 569,772, Aug. 21, 1990, abandoned, which is a continuation of Ser. No. 365,247, Jun. 12, 1989, filed as PCT/EP87/00769, Dec. 10, 1987, abandoned.

[30] Foreign Application Priority Data

Dec. 13, 1986 [DE] Fed. Rep. of Germany ....... 3642668

[51] Int. Cl.$^5$ ............................................. A61K 31/40
[52] U.S. Cl. ................................................... 514/419
[58] Field of Search ......................................... 514/419

[56] References Cited

U.S. PATENT DOCUMENTS

| 4,126,672 | 11/1978 | Sheth | 424/19 |
| 4,140,755 | 2/1979 | Sheth | 424/19 |
| 4,167,558 | 9/1979 | Sheth | 424/19 |
| 4,639,465 | 1/1987 | Pollack | 514/419 |

FOREIGN PATENT DOCUMENTS

| 0004040A1 | 3/1979 | European Pat. Off. . |
| 323873A1 | 3/1979 | Fed. Rep. of Germany . |
| 2113545A | 1/1982 | United Kingdom . |
| 2113546A | 1/1982 | United Kingdom . |

OTHER PUBLICATIONS

Unlisted Drugs, vol. 25, No. 9 (Sep. 1973).
Sicuteri, Advances in Pain Research and Therapy, vol. 1, pp. 872–880, Bonica and Albe-Fessard, Raven Press, New York, 1976.
Fernstrom, *Metabolism* 26:207–222 (1977).
Messing et al., *Pain* 4:1–21 (1977).
Moldofsky et al., *Pain* 5:65–71 (1978).
Dennis et al., *Experimental Neurology* 69:260–270 (1980).
Hosobuchi et al., *Pain* 9:161–169 (1980).
King, *J. Neurosurg.* 53:44–52 (1980).
Weil-Fugazz et al., *Pain* 9:319–325 (1980).
Buckett, *European J. of Pharm.* 69:281–290 (1981).
Conlay et al., *Neurosurgery* 10:524–529 (1982).
Seltzer et al., *Pain* 13:385–393 (1982).
Seltzer et al., *J. Psychiol. Res.* 17:181–186 (1982).
Hedaya, *J. Clin. Psychopharmacol.* 4:347–348 (1984).
Shpeen et al., *Oral Surgery* 58:446–449 (1984).
Braszko et al., *Biomed. Biochim. Acta* 44:1359–1368 (1985).
Seltzer, *J. of Endodontics* 11:449–453 (1985).
Millinger, *The J. of Cranimandibular Practive* 4:157–163 (1986).

*Primary Examiner*—S. J. Friedman
*Attorney, Agent, or Firm*—Fish & Richardson

[57] ABSTRACT

The invention relates to the use of L-tryptophane and a peripheral degradation inhibitor for L-tryptophan for the preparation of an analgesic drug for humans, the ratio by weight of L-tryptophan to the peripheral degradation inhibitor being from 3:1 to 10:1.

14 Claims, No Drawings

PAIN KILLER

This is a continuation of application Ser. No. 07/569,772, filed Aug. 21, 1990, now abandoned, which is a continuation of application Ser. No. 07/365,247, filed Jun. 12, 1989 now abandoned.

The invention relates to the use of L-tryptophan in combination with a peripheral degradation inhibitor as an analgesic agent.

In general pain and alleviation of pain constitute one of the great challenges to present-day medicine. The task is of particular importance in view of the fact that the economic damage caused by pain amounts to billions in view of about 3,000,000 people suffering from chronic pain alone in the Federal Republic of Germany.

The problem will become particularly clear in the treatment of persons suffering from chronic pain. On the one hand, the intake of the analgetically active substances as usually administered today is subject to narrow limits with respect to duration and side effects; on the other hand, as a rule, the goal of the treatment is not or only incompletely attained. The latter item frequently leads to a basically unallowed increase in dosage, even beyond the maximum limit involving side-effects such as hemorrhages, malignant tumors or damages to the liver. Moreover, drug dependence and addiction will often occur.

The recognition that acute pain and chronic pain are essentially distinguished from one another has led to turning away from the conventional therapy using analgesics which mostly provides only an insufficient effect. Hereby the activation of the nociceptive system is prevented through the inhibition of the prostaglandin synthesis upon lesions in tissue (acetylsalicylic acid, paracetamol, metamizol).

In contrast thereto, in chronic pain syndromes the pain becomes autonomic; thus, it does not make any more sense to block the prostaglandin synthesis. This leads to the use of thymoleptically and neuroleptically active drugs and drugs exerting central action (psychopharmaca, opiates et al.). In this case it is attempted to reach and to influence higher centers of the pain system. A good example herefor is phantom pain (pain which appears in a part of the body which does not exist anymore) or the altered pain threshold upon depressions. The considerable side-effects occurring thereupon as well as the low effect provided by this group of medicaments set narrow limits to the therapy also here.

In the course of modern pain research the structures of pain-conducting and pain-processing systems at all levels became more and more transparent and intelligible. In addition to the pain-sensitizing systems there have also been discovered systems of pain control which by means of chemical messenger substances (neurotransmitters) act upon the further conductance of pain pulses. One of the best-investigated neurotransmitters, including its pertinent neuronal systems, is serotonin. Serotonin acts at all neuronal levels by preferably inhibiting the further transmittance of pain and raising the pain threshold in combination with the opioid system. For this reason, serotinin would be an ideal physiological substance for inhibiting pain stimuli and affecting the pain processing and pain control mechanisms (limbic system and brain stem). Since, however, serotonin, due to considerable side-effects, cannot be directly administered to humans, a principle is generally utilized which is also employed with other neurotransmitters. In this case a biochemical precursor at a high concentration is given in the place of the neurotransmitter.

In general natural products or food constituents are used as precursors. By way of example, in the case of Parkinsonism L-dihydroxyphenylalanine (Dopa) is administered as the precursor in order to compensate for a systemic dopamine deficiency in the brain. However, the conventionally used precursors are already decomposed to a high degree peripherally, i.e. in blood and in the gastro-intestinal tract, to form the basically desired substances. Since the neurotransmitters as such cannot pass the blood-brain barriers, they will flood the periphery while they will virtually not enter the brain. This results in the known peripheral side-effects such as nausea, vomiting, heart and circulation malfunctions, changes in blood pressure etc. In order to avoid these side effects, L-Dopa is combined with peripheral degradation inhibitors. As a consequence, L-Dopa will be accumulated in blood and a sufficient amount will cross the blood-brain barriers; there, L-Dopa will be decomposed to form dopamine as desired.

If "pain" is the indication, even nowadays experiments with precursors are being carried out. Here, an excess amount of the food constituent tryptophan is administered in order to enhance the formation of the "anti-pain substance" serotonin in a biological-physiological manner.

However, due to a decomposition of tryptophan in the periphery an accumulation of serotonin results in the wrong place and, thus, in undesirable side-effects such as blood pressure crises, chronic diarrhea, bronchospasms, cardiac disorders, gastro-intestinal disorders etc.. Only a low amount of L-tryptophan will escape from the peripheral degradation and may uninhibitedly enter the central nervous system and there may be decomposed to form the desired transmitter. Attempts to administer as high amounts as possible of L-tryptophan in order to achieve an efficient accumulation of said amino acid failed because of the side-effects occurring thereupon.

It is for the above-mentioned reason that this natural product so far has not gained any practical importance in alleviation or treatment of pain. Thus, the use of a biologically-physiologically active substance in pain therapy failed. Instead, preference was attributed to the unphysiological principle of a manipulation of the pain-inhibiting system by means of psychopharmaca and centrally acting analgesics (opiates or the like).

Tryptophan is contained in most proteins in an amount of from 1 to 2%. Thus, this substance is a natural product occuring in usual human food. In total there are four routes of degradation of tryptophan. One of these degradation routes in the human organism leads via 5-hydroxytryptophan (5-HTP) after decarboxylation to 5-hydroxytryptamine (5-HT=serotonin). Serotonin is widely distributed in nature and is found in mammals in relatively high concentrations in the central nervous system, (hypothalamus, periaqueductal grey, central cavity grey, limbic system), in the spleen, the lungs, and in the argentaffinic cells of the intestinal tract. The concentration in whole blood is 0.1 to 0.3 $\mu g/ml$.

Serotonin peripherally acts onto the smooth muscles of the vessels, the respiration tract and the gastrointestinal tract etc.. Serotonin exerts a particularly important effect on the central nervous system. One of these effects relates to the regulation of pain.

Attempts to use L-tryptophan as an efficient analgesic drug have failed so far. According to S. Seltzer et al. (1982) L-tryptophan cannot influence the pain threshold (double blind study), however, it is capable to some extent (12%) to improve the pain tolerance limit, i.e. the limit at which the pain becomes intolerable. An improvement of the pain threshold, which means raising the threshold at which the stimulus is perceived as a pain stimulus, cannot be accomplished by L-tryptophan under normal conditions.

The use of the combination of L-Dopa and the specific decarboxylase inhibitor benserazide besides a hydrocolloid and some conventional auxiliary additives as a sustained-release formulation has been described in the DE-OS 32 32 873.

The use of L-tryptophan alone by itself for the treatment of chronic sleep disorders or depressive conditions has been realized by means of the L-Tryptophan A.S. tablets (Company A.S. Biologische und pharmazeutische Produkte GmbH), Tryptocompren ® (Cascan Company) and Kalma ® (Fresenius Company).

Sleep is a vitally important reduction of the state of consciousness in which reduction regeneration and restoration processes occur in almost all organs. There is a basic difference between sleep, unconsciousness and narcosis. While sleep is a physiological and reversible process, unconsciousness and narcosis are non-physiological processes which are not reversible at any time.

Pain, on the other hand, is an unpleasant sensation and emotional experience which is associated with tissue lesions or which is described with sensations as with tissue lesions, respectively (American Society for Pain Research). In this case pain has a physiological protective function as a signal of danger of injuries and stress situations to provoke necessary reactions.

L-Tryptophan alone was occasionally subjected to clinical testing with humans for the treatment of chronic pain. If L-tryptophan is used alone, at least about 3 g must be orally administered in order to cause an analgetic effect. This is because a large part of the L-tryptophan administered is peripherally decomposed, for example by the enzyme aromatic amino acid decarboxylase or other enzymes, before it can cross the blood-brain barrier and will become biologically effective upon conversion into serotonin. The amount of L-tryptophan passing the blood-brain barrier is considerably increased by blocking the peripheral aromatic amino acid decarboxylase and kynureninase.

It is the object of the present invention to provide a novel analgesic drug obtained by the use of L-tryptophan in combination with a peripheral degradation inhibitor.

It is a further object of the present invention to provide a sustained-release pharmaceutical formulation containing L-tryptophan and, more specifically, a peripheral decarboxylase inhibitor, which provides superior L-tryptophan blood levels and, thereby, constitutes a physiological analgesic drug with central action for humans in the case of chronic pain.

The above objects are attained by the use of L-tryptophan and of an inhibitor of the peripheral degradation of L-tryptophan for an analgesic drug for humans, wherein the ratio by weight of L-tryptophan to the peripheral degradation inhibitor is from 3:1 to 10:1.

An improvement of the transportation of L-tryptophan from the blood into the brain is possible due to the use of peripheral degradation inhibitors together with L-tryptophan.

L-Tryptophan (indolyl-3-alanine) is a physiological compound (an essential amino acid) which is employed for the treatment of insomnia, depressive syndromes (endogenous depressions) and psychotic side-effects of the L-Dopa therapy of Parkinsonism.

Peripheral degradation inhibitors, i.e., more specifically, decarboxylase inhibitors, are also substances which are clinically used, e.g. benserazide and carbidopa in the anti-Parkinson drugs Madopar ® and Nacom ®, respectively.

According to a preferred embodiment of the present invention a ratio by weight of L-tryptophan to the peripheral degradation inhibitor of from 3:1 to 5:1 is used.

Preferably, according to a further embodiment of the present invention there are employed decarboxylase inhibitors and/or kynureninase inhibitors as the peripheral degradation inhibitors for L-tryptophan.

Suitable decarboxylase inhibitors, within the scope of the present invention, are α-methyldopa, m-hydroxybenzylhydrazine, L-α-hydrazino-3,4-dihydroxy-α-methylhydrocinnamic acid (carbidopa) and $N^1$-D,L-serine-$N^2$(2,3,4-trihydroxybenzyl)-hydrazide hydrochloride (benserazide).

The serotonin content of human thrombocytes which are a model for central serotoninergic neurons is higher upon administration of the formulation according to the invention than that observed for formulations containing equal amounts of L-tryptophan but no benserazide. Moreover, the preparation according to the invention delays a drop in the level of the serotonin values of the thrombocytes as compared to the L-tryptophane preparations without decarboxylase inhibitor.

U.S. Pat. Nos. 4,126,672, 4,140,755, 4,167,558 and DE-OS 32 32 873 disclose formulations with sustained-release of the active ingredient upon oral application. These are capsules or tablettes which are hydrodynamically well balanced so that they have a specific weight of below 1 and will float on gastric juice having a specific weight of 1.004 to 1.010. The sustained release of active ingredient from these formulations is based on a mixture of active ingredients and one or more hydrophilic hydrocolloids.

Decarboxylase inhibitors act by inhibiting the enzyme aromatic amino acid decarboxylase. Moreover, the peripheral decarboxylase inhibitors employed, benserazide and carbidopa, are also inhibitors of kynureninase and of 2,3-dioxygenase. Upon simultaneous administration of L-tryptophan, this results in increased L-tryptophane values in plasma.

The formulations according to the invention are prepared according to generally known procedures. They consist of thoroughly mixing all of the components to form a homogeneous mixture and grinding, respectively, of the mixture to a relatively small particle size (e.g. 100 mesh).

The tablets are preferably prepared in such a manner that the active ingredients are first granulated and then compressed with tabletting machines to form tablets.

The present invention is further illustrated by the following Examples.

EXAMPLE 1

Formulation I

Sustained-release capsules having the following composition:

| Substance | mg/capsule |
| --- | --- |
| L-Tryptophan | 104.40 |
| Benserazide | 26.30 |
| Monocalcium phosphate | 14.80 |
| Hydrogenated cottonseed oil | 30.20 |
| Hydroxypropyl cellulose | 4.10 |
| Hydroxypropylmethyl cellulose | 114.90 |
| Mannitol | 20.10 |
| Talc | 14.80 |
| Total | 339.00 |

L-Tryptophane, benserazide, monocalcium phosphate and hydrogenated cottonseed oil were mixed together in the amounts as set forth above and ground. Then the obtained powder mixture was granulated with hydroxypropylcelluose which had been previously dissolved in alcohol. Then a ground mixture of hydroxypropylmethyl cellulose and mannitol was added to the granules. The extended mixture was subjected to a drying step, mixed with talc and filled into capsules.

Formulation II

Sustained-release tablets having the following composition position:

| Substance | mg/tablet |
| --- | --- |
| L-Tryptophan | 187.50 |
| Calcium carbonate | 45.80 |
| Carboxymethyl cellulose | 45.70 |
| Mannitol | 21.10 |
| Polyvinyl pyrrolidone | 9.20 |
| Hydroxypropylmethyl cellulose | 100.80 |
| Benserazide | 53.20 |
| Fumaric acid | 22.90 |
| Talc | 11.90 |
| Magnesium stearate | 2.80 |
| Total | 500.90 |

Using alcohol and part of the polyvinyl pyrrolidone granules were prepared from L-tryptophane, calcium carbonate, carboxymethyl cellulose and mannitol. Then hydroxypropyl methylcellulose was admixed to the granules, and the mixture was dried over night. Benserazide and fumaric acid were mixed and also granulated in alcohol using the residual polyvinyl pyrrolidone. Both kinds of granules were mixed with talc and magnesium stearate and processed to form tablets having a hardness of 5 to 8 Strong-Cobb units. The hardness of 12 Strong-Cobb units was not exceeded.

EXAMPLE 2

In vivo investigations

The formulations according to Example 1 were investigated for the behavior of thrombocytes of healthy test persons to serotonin. As has already been described, the physiological active substance in human organism is not L-tryptophan, but serotonin formed therefrom in central serotoninergic neurons. In the brain serotonin raises the pain threshold lowered upon chronic pain. The blood platelets are a recognized model for central serotoninergic neurons. As a rule, manipulations increasing the serotonin content in the blood platelets will also increase the serotonin content in central serotoninergic neurons, and the increase of the blood platelet 5-HT content is correlated with reduced pain centrally caused.

The test persons took (re-calculated) 1 g of L-tryptophane and 250 mg of benserazide of the formulations of Example 1 in one oral daily dose in the morning. Prior to the intake of the drug and in intervals of half an hour each until 6 hours after, blood samples were taken from the test persons, and the serotonin content of the blood platelets of the individual samples was determined by spectrofluorometry. In a second test carried out three weeks after the above-described test the same test persons were given 1 g of L-tryptophan without benserazide. In both time tests the serotonin level of the blood platelets increased under the L-tryptophan load; however, in the test using benserazide in combination the serotonin content on the average was higher by about 40% than that of the test in the absence of benserazide. Moreover, in the test in the presence of benserazide the effect was detectable still more than four hours after the begin of the test, whereas in the absence of benserazide said effect was detectable only until two hours after the begin of the test.

We claim:

1. The method of reducing pain in a human patient which comprises administering to said patient an analgesically effective dose of a composition comprising L-tryptophan together with a member of the group consisting of α-methyldopa, m-hydroxybenzylhydrazine, $N^1$-D,L-serine-$N^2$-(2,3,4-trihydroxybenzyl) hydrazine, L-α-hydrazino-α-methyl-3,4-dihydroxyhydrocinnamic acid and mixtures thereof, the weight ratio of L-tryptophan to said member being from 3:1 to 10:1, said composition being administered in the form of a sustained release formulation.

2. The method as claimed in claim 1 in which said ratio is from 3:1 to 5:1.

3. The method as claimed in claim 1 or 2 in which said member in $N^1$-D,L-serine-$N^2$-(2,3,4-trihydroxybenzyl)-hydrazide.

4. The method as claimed in claim 1 or 2 wherein the composition contains from 5 to 80% by weight of a hydrocolloid or of a mixture of hydrocolloids, up to 60% by solid or a mixture of solids, and up to 80% by weight of inert edible pharmaceutical excipients, and the composition has been hydrodynamically balanced so that it assumes a specific weight below 1 when in contact with the gastric juice so that it floats in the gastric juice.

5. An analgesic composition in the form of a sustained release formulation comprising L-tryptophan together with a member of the group consisting of α-methyldopa, m-hydroxybenzylhydrazine, $N^1$-D,L-serine-$N^2$-(2,3,4,-trihydroxybenzyl) hydrazine, L-α-hydrazine-α-methyl-3,4-dihydroxyhydrocinnamic acid and mixtures thereof, the weight ratio of L-tryptophan to said member being from 3:1 to 10:1.

6. An analgesic composition as claimed in claim 5 in which said ratio is from 3:1 to 5:1.

7. A composition as claimed in claim 5 or 6 in which said member is $N^1$-D,L-serine-$N^2$-(2,3,4-trihydroxybenzyl)hydrazine.

8. The composition as claimed in claim 5 or 6 wherein the composition contains from 5 to 80% by weight of a hydrocolloid or of a mixture of hydrocolloids, up to 60% by weight of a solid or of a mixture of solids, and up to 80% by weight of inert edible pharmaceutical excipients, and the composition has been hydrodynamically balanced so that it assumes a specific weight below 1 when in contact with the gastric juice so that it floats in the gastric juice.

9. An analgesic composition in the form of a sustained release formulation comprising L-tryptophan and a peripheral degradation inhibitor for L-tryptophan, the weight ratio of L-tryptophan to the peripheral degradation inhibitor being from 3:1 to 10:1.

10. An analgesic composition as claimed in claim 9, in which said ratio is from 3:1 to 5:1.

11. An analgesic composition as claimed in claim 9 or 10, in which a preipheral decarboxylase inhibitor and/or a kynureninase inhibitor is used as the peripheral degradation inhibitor for L-tryptophan.

12. An analgesic composition as claimed in claim 11, in which the peripheral decarboxylase inhibitor has been selected from the group consisting of 60 -methyldopa, m-hydroxybenzylhydrazine, $N^1$-D,L-serine-$N^2$-(2,3,4-trihydroxybenzyl)-hydrazide, L-α-hydrazino-3,4-dihydroxy-α-methylhydrocinnamic acid and mixtures thereof.

13. An analgesic composition as claimed in claim 12, wherein the composition contains from 5 to 80% by weight of a hydrocolloid or a mixture of hydrocolloids, up to 60% by weight of a solid or a mixture of solids, and up to 80% by weight of inert edible pharmaceutical excipients and the composition has been hydrodynamically balanced so that it assumes a specific weight below 1 when in contact with the gastric juice so that it floats on the gastric juice.

14. The method of reducing pain in a human patient which comprises administering to said patient an analgesic effective dose of the composition in claim 9, 10, 11, 12 or 13.

* * * * *